United States Patent [19]

Ramalingham

[11] Patent Number: 4,864,051

[45] Date of Patent: Sep. 5, 1989

[54] PROCESS FOR PREPARING 2-METHOXYISOBUTYLISONITRILE

[75] Inventor: Kondareddiar Ramalingham, North Brunswick, N.J.

[73] Assignee: E. R. Squibb & Sons, Inc., Princeton, N.J.

[21] Appl. No.: 239,726

[22] Filed: Sep. 2, 1988

[51] Int. Cl.$^4$ ............................................. C07C 119/02
[52] U.S. Cl. .................................................... 558/302
[58] Field of Search ........................................ 558/302

[56] References Cited

FOREIGN PATENT DOCUMENTS 0233368  6/1987  European Pat. Off.

OTHER PUBLICATIONS

Noller, "Chemistry of Organic Compounds", p. 254, 3rd Ed., 1965, W. B. Saunders C; Phila & London.

Abrams, M. J.; Davison, A.; Jones. A. G.; Costello, C. E.; Pang, H., Synthesis and Characterization of Hexakis (Alkyl Isocyanide) and Hexakis (Aryl Isocyanide) Complexes of Technetium (I), (1983), Inorg. Chem., 22, pp. 2798–2800.

Abrams, M. J.; Davison, A.; Brodack, J. W.; Jones A. G.; Faggiani, R.; Lock, C. L. The Preparation of Technetium(III) Compound in Aqueous Media, J. Labbelled Compd. Radiopharm., (1982), 14, pp. 1596–1597.

Mousa, S. A.; Maina, M; Williams S. J., Retention of RP-30 in the Heart May be Due to Binding to a Cytosolic Protein. Scientific Papers, vol. 28, pp. 619–620, (1987).

Mousa, S. A.; Cooney, J. M.; Williams, S. J.; Regional Myocardial Distribution of RP-30 in Animal Models of Myocardial Ischemia and Reperfusion; J. Nucl. Med., (1987), vol. 28. P. 620.

Taillefer, R.; Laflamme, L.; Dupras, G.; Picard, M.; Phaneuf, D. C., Leveille, J., Myocardial Perfusion Imaging with 99mTc-Methoxyisobutyl-Isonitril (MIBI), Eur. Nucl. Med., (1988), 13, pp. 515–522.

Weber, W. P.; Gokel, G. W.; Ugi, I. K., Phase Transfer Catalysis in the Hofmann Carbylamine Reaction, Angew. Chem. Int. Ed. Engl., (1972), II, p. 530.

Schuster, R. E.; Scott, J. E.; Casanova, J., Methyl Isocyanide; Organic Synthesis, Collect, vol. V. (1973), 772–774.

Ugi, I., Isocyanide Synthesis with Diphosgene; Skorna, G. Agnew. Chem. Int. Ed. Engl. (1977), 16, pp. 259–260.

Casanova, J.; Schuster, R. E.; Werner, N. D., Synthesis of Aliphatic Isocyanides; J. Chem. Soc., (1963), 4280–4281.

Angelberger, P.; Zbiral, E., Synthesis, Radiochromatography and Biodistribution of Tc99m-Hexakis-(Methoxyisonitrile)-Technetium(I) Complexs, [Ber]OEFZS, (1987) 4411.

Navalokina, R. A.; Zil'berman, E. N., Production of Unsymmetrical Ethers from 2-Hydroxyisobutyronitrile and Various Alcohols, J. Org. Chem. USSR (Engl. Trans.), (1980) 16; pp. 1382–1386.

Primary Examiner—Joseph Paul Brust
Attorney, Agent, or Firm—Donald J. Barrack; Stephen Venetianer

[57] ABSTRACT

A new process for preparing 2-methoxyisobutylisonitrile is described. 2-methoxyisobutylisonitrile is used in the preparation of Tc-99m hexakis (2-methoxyisobutylisonitrile). This cationic complex is useful as a myocardial perfusion agent.

4 Claims, No Drawings

PROCESS FOR PREPARING 2-METHOXYISOBUTYLISONITRILE

BACKGROUND OF THE INVENTION 2-methoxyisobutylisonitrile is a key starting material in the preparation of Tc-99 m hexakis (2-methoxyisobutylisonitrile). The preparation of Tc-99 m hexakis (2-methoxyisobutylisonitrile) from 2-methoxyisobutylnitrile has been described by Angelberger, P.; Zbiral, E.; [Ber] OEFZS., 1987, 44. This cationic complex has been reported to be clinically useful as a myocardial perfusion agent by Mousa, S. A.; Maina, M.; Brown, B. A.; Williams, S. J., *J. Nucl. Med.*, 1987, 28, 619 (Abstr.). Mousa, S. A.; Cooney, J. M.; Williams, S. J., *J. Nucl. Med.*, 1987, 28, 620 (Abstr.). Taillefer, R.; Laflamme, L.; Dupras G.; Picard, M.; Phaneuf, D. C.; Leveille, J., *Eur. Nucl. Med.*, 1988, 13 515. The synthesis of hexakis (alkyl isocyanide) and hexakis (arylisocyanide) complexes of technetium(I) have been reported by Abrams, M. J.; Davison, A.; Jones, A. G.; Costello, C. E.; Pang, H., *Inorg. Chem.*, 1983, 22, 2798. Abrams, M. J.; Davison, A.; Brodack, J. W.; Jones, A. G.; Faggiani, R.; Lock, C. J. L., *J. Labelled Compd. Radiopharm*, 1982, 14, 1596.

The synthesis of various isocyanides have been reported by Weber, W. P.; Gokel, G.W.; Ugi, I. K., *Angew. Chem., Int. Ed. Engl.* 1972, II, 530. Schuster, R. E.; Scott, J. E.; Casanova, J. Jr., "Organic Synthesis", Wiley; New York, *Collect. Vol. V*, 1973, 772–774.. Giselher, S.; Ugi, I., *Angew. Chem., Int. Ed. Engl.* 1977, 16 259. Casanova, J. Jr.; Schuster, R. E.; Werner, N. D., *J. Chem. Soc.*, 1963, 4280.

SUMMARY OF THE INVENTION

It has now been discovered that 2-methoxyisobutylisonitrile can be prepared from commercially available 2-hydroxyisobutyronitrile in a four step synthesis with a yield of 26%. A synthesis of 2-methoxyisobutylisonitrile has been reported in Angelberger, P.; Zbiral, E., [Ber]OEFZS., 1987, 44, which involves six steps and with no reported yields. European Patent Application No. 233,368 discloses a five step process with an overall yield of 8.1%

The process of this invention can be represented by the following diagram:

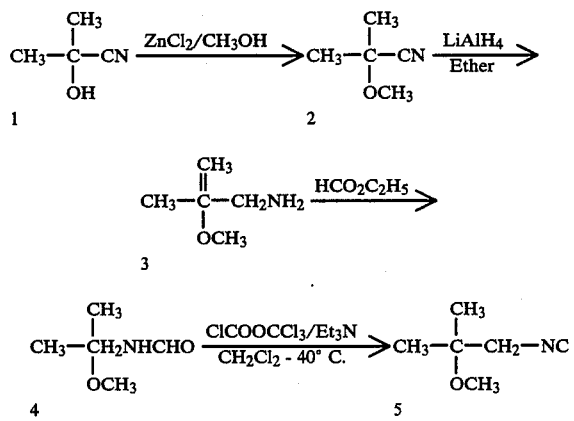

DETAILED DESCRIPTION OF THE INVENTION

Etherification of the nitrile compound 1 is effected with anhydrous methanol and freshly fused zinc chloride to give the compound 2. Reduction of compound 2 with lithium aluminum hydride in ether produces the amine compound 3 in good yield in about 8 hours. N-Formylation of compound 3 with ethyl formate and a catalytic amount of p-toluenesulphonic acid produces the amide compound 4. The amide compound 4 is isolated in high yield after distillation. In the final conversion to isonitrile the amide compound 4 is treated with trichloromethylchloroformate ("diphosgene") at −40° C. in the presence of triethylamine. Isolation of compound 5 is easily achieved after distillation. Compound 5 is reasonably stable and can be stored in a refrigerator for six months.

The following examples are specific embodiments of this invention.

EXAMPLE 1

2-Methoxyisobutyronitrile

To a solution of freshly fused zinc chloride (149 g, 1.09 mol) in anhydrous methanol (100 ml) was added 2-hydroxyisobutyronitrile (commercially available) (100 ml, 93 g, 1.09 mol). The mixture was heated (60° C.) in an oil bath for 12 hours. After cooling to room temperature, the reaction mixture was poured onto ice. It was then extracted with ether (3×200 ml) and the combined extracts dried ($Na_2SO_4$). Removal of the solvent and distillation of the residue afforded 52 g (51%) of 2-methoxyisobutyronitrile, bp 117°–118° C.

$^1$H-NMR (CDCl$_3$) 1.31 (s, 6H (CH$_3$)$_2$C), 3.25 (s, 3H, OCH$_3$). $^{13}$C-NMR (CDCl$_3$) 26.23 (CH$_3$—), 53.12 (OCH$_3$), 71.12 (—C—), 120.28 (CN).

EXAMPLE 2

2-Methoxyisobutylamine

To a well stirred slurry of lithium aluminum hydride (9.0 g, 0.24 mol) in dry ether (500 ml) was added dropwise a solution of 2-methoxyisobutyronitrile (19.8 g, 0.2 mol) in dry ether (150 ml). The mixture was stirred under reflux for 8 hours. Excess hydride was carefully destroyed by the dropwise addition of water. The mixture was filtered and the filter cake washed with ether (6×150 ml). The combined ether solution was dried (Na$_2$SO$_4$). After removal of ether, the residual liquid was distilled to give 16.8 g (82.0%) of the title compound, bp 124°–125° C.

$^1$H-NMR (CDCl$_3$) 1.16 (s, 6H, (CH$_3$)$_2$C), 1.6 (s, 2H, NH$_2$), 2.65 (s, 2H, CH$_2$), 3.26 (s, 3H, OCH$_3$). $^{13}$C-NMR (CDCl$_3$) 22.31 (CH$_3$), 49.15 (CH$_2$), 50.38 OCH$_3$), 74.77 (C) MS: m/e 104 (M+1).

Anal. Calculated for C$_5$H$_{13}$NO: C, 58:21; H, 12.70; N, 13.58. Found: C, 58.17; H, 12.84; N, 13.74.

EXAMPLE 3

N-Formyl-2-methoxyisobutylamine

To a stirred solution of 2-methoxyisobutylamine (16.4 g, 0.16 mol) and a catalytic amount of p-toluenesulphonic acid (75 mg) at 0° C. was added slowly ethylformate (11.79 g, 12.92 ml, 0.16 mol). After the slightly exothermic reaction ceased, the solution was refluxed for 16 hours, and distilled through a Vigreux column to give 19.36 g (93%) of N-formyl-2-methoxyisobutylamine, bp 74° C./15 mm.

$^1$H-NMR (CDCl$_3$) 1.13 (s, 6H, (CH$_3$)$_2$C), 3.15 (s, 3H, OCH$_3$, 3.27 (d, 2H J=5.8 Hz, CH$_2$) 6.0 (bs, 1H, NH), 8.19 (s, 1H, CHO).

$^{13}$C-NMR (CDCl$_3$) 22.65 (CH$_3$), 46.26 (CH$_2$) 49.60 (OCH$_3$), 161.53 (CHO). MS: m/e 132 (M+1)

Anal. Calculated for C$_6$H$_{13}$NO$_2$·1H$_2$O: C, 54.08; H, 10.01; N, 10.51. Found: C, 53.90; H, 9.85; N, 10.59.

EXAMPLE 4

2-Methoxyisobutylisonitrile

To a cooled (−40° C.) solution of N-formyl-2-methoxyisobutylamine (9.0 g, 0.69 mol) and triethylamine (19.5 ml, 14.16 g, 0.14 mol) in dry dichloromethane (100 ml) was added dropwise trichloromethylchloroformate ("diphosgene") (4.15 ml, 6.8 g, 0.035 mol) in dry dichloromethane (50 ml) over a period of 1 hour. After the addition was complete, the temperature of the reaction mixture was allowed to rise to 0° C. and stirred for 1 hour, and at reflux temperature for 0.5 hour. Water (25 ml) was added and the organic layer separated. The organic layer was washed with a saturated solution of sodium bicarbonate (25 ml), water (25 ml) and dried (Na$_2$SO$_4$). Evaporation of the methylene chloride left a dark brown liquid. The dark brown liquid obtained was distilled under vacuum to give 5.2 g (66.7%) of the title compound as a colorless liquid b.p. 60°–61° C./22 mm.

$^1$H-NMR (CDCl$_3$) 1.25 (s, 6H), (CH$_3$)$_2$C), 3.22 (s, 3H, OCH$_3$), 3.38 (m, 2H, CH$_2$).

$^{13}$C-NMR (CDCl$_3$ 22.23 (CH$_3$), 49.69 (OCH$_3$), 50.32 (CH$_2$), 73.06 (C), 157.49 (NC) MS: m/e 114 (M+1).

Anal. Calculated for C$_6$H$_{11}$NO: C, 63.68; H, 9.80; N, 12.38. Found: C, 63.72; H, 9.89; N, 12.70.

What is claimed is:

1. A process for preparing a compound of the formula

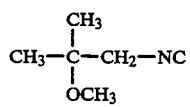

which comprises the steps of (A) methylating a compound of formula

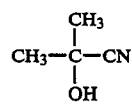

with an anhydrous methylating agent in the presence of zinc chloride at a temperature of about 60° C. for about twelve hours to form a compound of the formula

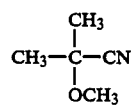

and (B) reducing the above ether with a reducing agent in the presence of ether for about eight hours to form a compound of the formula

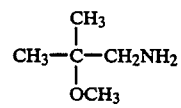

and (C) formylating the above amine with a formylating agent in the presence of a catalytic amount of p-toluenesulphonic acid at about 0° C. for about sixteen hours to form a compound of the formula

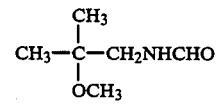

and (D) reacting the above amide with trichloromethylchloroformate in the presence of triethylamine at a temperature of about minus 40° C. for about one hour to form the desired isonitrile.

2. A process according to claim 1 wherein the methylating agent is methanol in the presence of zinc chloride.

3. A process according to claim 1 wherein the reducing agent is lithiumaluminumhydride.

4. A process according to claim 1 wherein the formylating agent is ethyl formate.

* * * * *